US010557796B2

(12) United States Patent
Olschewski et al.

(10) Patent No.: US 10,557,796 B2
(45) Date of Patent: Feb. 11, 2020

(54) METHOD AND DEVICE FOR DETERMINING THE TRANSMITTANCE OF A FLAT GLASS SUBSTRATE

(71) Applicant: Cibite AG, Donauwörth (DE)

(72) Inventors: Dieter Olschewski, Donauwörth (DE); Ina Döhring, Augsburg (DE); Peter Lüke, Kaisheim (DE)

(73) Assignee: Cibite AG, Donauwörth (DE)

( * ) Notice: Subject to any disclaimer, the term of this patent is extended or adjusted under 35 U.S.C. 154(b) by 25 days.

(21) Appl. No.: 15/520,444

(22) PCT Filed: Oct. 20, 2015

(86) PCT No.: PCT/EP2015/074249
§ 371 (c)(1),
(2) Date: Sep. 28, 2017

(87) PCT Pub. No.: WO2016/062711
PCT Pub. Date: Apr. 28, 2016

(65) Prior Publication Data
US 2018/0128740 A1 May 10, 2018

(30) Foreign Application Priority Data
Oct. 21, 2014 (DE) .......................... 10 2014 115 317

(51) Int. Cl.
*G01N 21/84* (2006.01)
*G01N 21/59* (2006.01)
*G01N 21/896* (2006.01)

(52) U.S. Cl.
CPC .......... *G01N 21/59* (2013.01); *G01N 21/896* (2013.01); *G01N 2021/8416* (2013.01); *G01N 2201/06126* (2013.01)

(58) Field of Classification Search
CPC ................. G01N 21/59; G01N 21/896; G01N 2201/06126; G01N 2021/8416; G01N 21/8903; G01N 21/956
(Continued)

(56) References Cited

U.S. PATENT DOCUMENTS

2003/0169433 A1* 9/2003 Koele ............... A61F 13/15772
356/614
2010/0033735 A1* 2/2010 Sakai ................. G01B 11/0633
356/632
(Continued)

FOREIGN PATENT DOCUMENTS

CN 102944563 2/2013
EP 2472251 7/2012
(Continued)

OTHER PUBLICATIONS

International Search Report and the Written Opinion Dated Feb. 23, 2016 From the International Searching Authority Re. Application No. PCT/EP2015/074249 and Its Translation of Search Report Into English.

*Primary Examiner* — Isiaka O Akanbi

(57) ABSTRACT

A method and an associated device for determining the transmittance of a flat-glass substrate with a measuring device, with which light of at least one light source is guided from one side of the flat-glass substrate through the flat-glass substrate to the opposite side of the flat-glass substrate, where it is captured by at least one receiving unit and the transmittance of the flat-glass substrate is determined by means of a comparison between the intensity of the light emitted by the light source and the light incident upon the receiving unit. The light source is a surface-like diffuse light source, and the receiving unit comprises at least one spatially resolving receiver. By evaluating brightness values in the measuring image of the spatially resolving receiver, the transmittance is determined in a spatially resolved manner in a partial surface of the flat-glass substrate, which is covered by the measuring image.

15 Claims, 1 Drawing Sheet

(58) Field of Classification Search
USPC ........ 356/237.2–237.6, 239.1, 601–615, 632
See application file for complete search history.

(56) References Cited

U.S. PATENT DOCUMENTS

| | | | | |
|---|---|---|---|---|
| 2013/0077101 A1* | 3/2013 | Sharoni | ................... | G03F 1/144 |
| | | | | 356/625 |
| 2013/0188188 A1* | 7/2013 | Kwon | ................... | G01N 21/59 |
| | | | | 356/432 |
| 2013/0222804 A1* | 8/2013 | Kim | ................ | G01N 21/59 |
| | | | | 356/432 |

FOREIGN PATENT DOCUMENTS

| | | | | |
|---|---|---|---|---|
| EP | 2615446 | 7/2013 | | |
| JP | 08-327561 | 12/1996 | | |
| JP | 2006-266933 | 10/2006 | | |
| JP | 2009-236493 | 10/2009 | | |
| JP | 2009236493 A * | 10/2009 | ........... | G01N 21/892 |
| WO | WO 2016/062711 | 4/2016 | | |

\* cited by examiner

METHOD AND DEVICE FOR DETERMINING THE TRANSMITTANCE OF A FLAT GLASS SUBSTRATE

RELATED APPLICATIONS

This application is a National Phase of PCT Patent Application No. PCT/EP2015/074249 having International filing date of Oct. 20, 2015, which claims the benefit of priority of German Patent Application No. 10 2014 115 317.0 filed on Oct. 21, 2014. The contents of the above applications are all incorporated by reference as if fully set forth herein in their entirety.

FIELD AND BACKGROUND OF THE INVENTION

The invention relates to a method and a device for determining the transmittance of a flat-glass substrate with a measuring device, with which light of at least one light source is guided from one side of the flat-glass substrate through the flat-glass substrate to the opposite side of the flat-glass substrate, where it is captured by at least one receiving unit. The transmittance of the flat-glass substrate can then be determined by means of a comparison between the intensity of the light emitted by the light source and the light incident upon the receiving unit.

In the manufacture of flat glass, a continuous transmittance must be achieved as one of various quality requirements. The thickness of the glass, for example, is another essential parameter. Particularly when using flat glass as solar glass, which is a special glass for thermal solar collectors and photovoltaics, a continuous transmittance has to be observed. In order to be able to use the incident solar radiation optimally, as high a transmittance as possible of the supported glass layer has to be ensured.

In this case, flat glass provided for use as solar glass has particularly high requirements with respect to continuous homogeneity. With regard to flat glass as such, a distinction is made between float glass and rolled glass, the type of glass depending on the production process chosen in each case. Both types of glass are used as solar glass, it being possible to manufacture planar glass in a float process, and structured glass (structural glass) in a rolling process. Typically, both production processes are endless continuous processes in which the glass melt is permanently pulled in a flat manner onto a tin bath or rolled through rotating rollers. The glass is cut to size only after passing through a cooling system.

SUMMARY OF THE INVENTION:

The process of manufacturing solar glass requires a secured, constant transmittance over the entire production width. Deviations therefrom directly result in quality problems in processing the glass plates into solar modules. The structural glass often used for manufacturing solar modules is cast glass in which the structure is impressed by rotating rollers. Already the temperature of these rollers and their running accuracy affect the glass thickness and transmittance. In addition, parameters such as the inhomogeneity of the glass mixture or impurities, which may lead to different structures, are relevant.

Because the solar cells and the glass cover are irreversibly connected to each other in photovoltaic module production, for example, a poor glass quality results in an additional amount of rejects of expensive photovoltaic cells. At present, an insufficient transmittance can only be discovered during the output inspection of the finished solar glass product, or frequently only in the solar module itself. Therefore, the reject costs are particularly high in this case. In that case, the coated glass constitutes special waste, and empirically, the reject rate is in the high single-digit percentage range. This great microeconomic and macroeconomic damage and the simultaneous destruction of resources (among other things, silicon in the glass and solar cell production) can only be reduced by detecting flaws as early as possible during glass production.

Measuring methods for verifying the transmittance, by means of which the parameters to be monitored can be randomly verified, were already developed. In this case, spectral photometers are commonly used in which the wavelength of the incident light beam varies and the transmitted proportion is registered as a function of the wavelength. Optionally, the angular dependence of the incidence of the light is also taken into account in this case. However, such measurements require much effort and are usually only carried out under laboratory conditions, and are unsuitable for use in the production process. Furthermore, they usually are point measurements with which it is not possible to inspect the entire surface of a flat-glass substrate.

Particularly in the field of solar glass, the influence of the angle of incidence of light is considerable because at a smaller angle, larger proportions of light are reflected and absorption increases due to the greater penetration distances. However, the angle of incidence changes naturally over the course of the day and the year. Therefore, the manufacturers of solar glass make increased efforts to increase the effectivity of the solar cells even for flat angles of incidence, by means of measures such as anti-reflection coatings and structured surfaces. However, the necessary measuring accuracy of measuring methods used for verifying the transmittance so far does not match this development. Particularly the transmittance of structural glass with structures incorporated into the surface cannot be reliably inspected with the known measuring methods.

Therefore, it is the object of the invention to provide a method and a device for verifying the transmittance of a flat-glass substrate with which an extensive transmission measurement can be carried out that can be integrated into the production process. In particular, the method and the device are in this case supposed to be suitable for verifying the transmittance of structural glass.

According to the invention, this object is achieved by means of a method according to the independent claim 1. Advantageous embodiments of this method are apparent from the dependent claims 2-11. Furthermore, the object is achieved by means of a device according to the independent claim 12. Advantageous embodiments of the device are apparent from claims 13-15.

It must be noted that the features cited individually in the claims can be combined with each other in any technologically meaningful manner and represent other embodiments of the invention. The description, in particular in connection with the figures, additionally characterizes and specifies the invention.

The inventive method according to claim 1 is suitable for determining the transmittance of a flat-glass substrate with a measuring device, with which light of at least one light source is guided from one side of the flat-glass substrate through the flat-glass substrate to the opposite side of the flat-glass substrate, where it is captured by at least one receiving unit. The transmittance of the flat-glass substrate is determined by means of a comparison between the intensity of the light emitted by the light source and the light incident upon the receiving unit. According to the invention, the light source used is a surface-like diffuse light source, and the receiving unit comprises at least one spatially resolving receiver, between which the flat-glass substrate is positioned. By evaluating brightness values in the measuring image of the spatially resolving receiver, the transmittance is determined in a spatially resolved manner in a partial surface of the flat-glass substrate, which is covered by the measuring image.

Light can thus be transmitted through a surface of the flat-glass substrate in a homogeneous manner by means of the surface-like diffuse light source, and using one or several spatially resolving receivers, it is possible to also determine, by means of this light, the transmittance in a spatially resolved manner within the partial surface of the flat-glass substrate which is covered by the measuring image of the respective receiver.

Preferably, a camera is used as the spatially resolving receiver. This may be a camera with a CCD or CMOS chip, for example. With this camera, a measuring image can be prepared that covers, for example, a partial surface with an order of magnitude of 5×10 cm or 10×20 cm on the flat-glass substrate.

In order to increase the accuracy in the determination of the transmittance, it is preferably provided that image editing is carried out in the measuring image of the spatially resolving receiver. Then, the transmittance is determined by means of the brightness values after the image editing of the measuring image. Particularly for measuring points in the image, the image editing may include an averaging process for brightness values over several points of at least a portion of the measuring image. By using a surface-like diffuse light source in accordance with the invention, a superposition of a plurality of point sources occurs, thus resulting in a rather more statistical measured value, which is produced by the superposition of the various point sources and passages through the glass. For the invention, it is presumed that this measured value should be the same everywhere on average.

The portions within the measuring image used for the averaging process should preferably be chosen to be large enough so that possible deflections of the light while passing through the flat-glass substrate within a portion can be captured and included into the averaging process. Therefore, when using the method for inspecting structural glass, a portion of the measuring image used for the averaging process, advantageously, is larger than dimensions of structures in the surface of the flat-glass substrate. If, for example, pyramid-like structures are incorporated into the surface, the portions for the averaging process should be larger than the extent of the individual structures. Thus, deflections of the light by the structures can be taken into account by means of suitable image editing. Thus, the invention makes it possible, in particular, to also determine the transmittance of structural glass with sufficient accuracy.

Therefore, the method can be used universally for all flat-glass production methods, types of flat glass and applications of flat glass. In particular, it is suitable for verifying the transmittance of structural glass. In particular for solar glass production, the detected transmittance of float glass should be ≥90%. By structuring and coating the surface, an improvement of in each case up to 3% can be achieved. Since the specifications are, as a rule, accurate to 0.1%, the intended measuring accuracy should be ≤0.1%.

In this case, the focus of the invention is, in particular, on a measurement for quality assurance, i.e. the primary goal of the system is to ensure a constant quality. Various factors, including, for example, bubbles in the glass or an increased absorption in the glass itself, may be the cause for a reduced transmission. Increased absorption may be caused by impurities in the glass. In this case, iron-containing admixtures are typical, but there are also other mineral impurities that are capable of increasing the absorption in the glass. The thickness of the glass also has an influence on the transmittance; however, this influence is relatively small.

Impurities in the glass, which cause a reduction in transmittance due to absorption, are located for quality assurance. Based on known transmission spectra of glass, this goal can be achieved by measuring the transmittance for individual selected wavelengths, for example, which are realized by means of a surface-like diffuse light source with monochromatic or narrow-band light sources. The wavelengths chosen are preferably those that are selectively absorbed by potential impurities in the glass. The receiving unit is in that case tuned to the chosen wavelengths. As an alternative or addition to measurements with monochromatic of different wavelengths, a measurement with white light may also be carried out.

In the process, an absolute value for the transmittance may be determined. For a quality assurance process, however, it may also be sufficient to merely determine the deviation of the transmission from a target value and to thus verify the transmittance. In one embodiment of the invention, a verification of the transmittance is thus carried out by means of a comparison of a transmittance determined by the measuring device with a target transmittance. Basically, a target-actual comparison of the transmittance is then carried out.

The method may be carried out with a stationary measuring device into which a flat-glass substrate is temporarily introduced. Given an appropriate extent of the light source and a receiving unit with, for example, a plurality of receivers, the transmittance can thus be verified within a larger area of a flat-glass substrate. In a preferred embodiment of the invention, however, the flat-glass substrate and the measuring device are continuously moved relative to one another in such a manner that over the course of this movement, the receiving unit captures the light passage through different partial areas of the flat-glass substrate. In this manner, a flat-glass substrate can be inspected in its entirety if a movably configured measuring device scans the entire surface of a substrate, for example. In order to avoid movable components of a measuring device, however, it was found to be advantageous if the latter is substantially stationary and the flat-glass substrate is moved relative to the measuring device, in order to also scan the entire surface of a substrate in this manner.

In one embodiment of the invention, in order to integrate the method into the production process of flat-glass production in an advantageous manner, it is provided, in particular, that the measuring device is stationary, whereas the flat-glass substrate is continuously moved through between the light source and the receiving unit. In this case, the measuring device can be configured as a kind of portal through which a continuously produced glass sheet is permanently guided between the light source and the receiving unit.

Preferably, the flat-glass substrate has an extent with the width B transverse to the direction of the relative movement between the measuring device and the flat-glass substrate, with the light source transmitting light through the flat-glass substrate over the entire width B. A correspondingly configured receiving unit can then capture the light passing through a strip through the flat-glass substrate that extends over the entire width B of the flat-glass substrate. A type of line scan can be performed in this manner, whereby a full-surface inspection of a glass sheet can be carried out continuously in a flat-glass substrate moved constantly through the measuring device.

In particular, the receiving unit has several receivers (cameras) for this purpose, which are configured for capturing light of the light source and whose measuring images are combined into an image of a planar area of the flat-glass substrate by an image processing unit. In this manner, a greater partial surface of the flat-glass substrate can be inspected. For a line scan, the receivers of the receiving unit are disposed next to one another, for example, and their measuring images are combined into an image of a strip of the flat-glass substrate extending over the entire width B. In any case, it is advantageous here if in this case, the measuring images of the receivers overlap in some areas. Thereby, the accuracy of the determination of the transmittance can be increased if, for example, brightness values of one and the same point in two overlapping images are compared to each other and thus verified, if possible. In the case of deviating brightness values for a single point, an averaging process may also be carried out. The overlapping measuring images may also be used for a self-calibration of the measuring system with several receivers.

On the whole, the invention makes it possible to carry out a transmission measurement in an extensive manner within a continuous production process for flat glass, and not as a single measurement on the cut goods. However, the single measurement on cut goods is not excluded; rather, the invention entails the aforementioned advantages with respect to an extensive verification of the transmittance also for this embodiment.

In particular, it is also possible to measure the transmission directly in the production process and thus immediately intervene in the running manufacturing process. Thus, the method makes it possible to conform to the high requirements for solar glass, for example, already during the production. The reject rate of coated glass, and subsequently in photovoltaic and collector modules, is reduced in a sustained manner by a continuous transmission measurement. It is therefore an important ecological and economic advantage that the amount of rejects in production and in further processing (coating or preparation of composite glass) can be significantly reduced. This results in considerable savings in reject and disposal costs.

In this case, a use under production conditions is possible, which particularly includes high temperatures and extraneous light (e.g. lighting, industrial trucks). By using modulated light, the influence of extraneous light can be eliminated, for example.

In one embodiment of the invention, it is additionally provided that light of the light source is captured by the receiving unit in at least one area next to the flat-glass substrate without passing through the flat-glass substrate. For this purpose, the light source may be configured to be wider than the flat-glass substrate to be inspected, so that areas to the left and to the right of a glass sheet, for example, are also illuminated. In that case, the receiving unit is configured in such a way that it is capable of capturing also this light. Thus, a zero measurement without a medium, which corresponds to a transmission of 100%, can be carried out in the border area of the flat-glass substrate. This zero measurement reflects changes in the external conditions that may occur during continuous operation of the measuring device and which must be taken into account during calibration. The light of the light source captured by the receiving unit without passing through the flat-glass substrate can therefore, in particular, be used as a reference value for the calibration of the measuring device.

Preferably, the calibration takes place in the form of a self-calibration of the system. In one embodiment of the invention, this can also take place continuously during the verification of the transmittance, because the zero measurement next to the substrate can be carried out constantly. Thus, the production process of a glass sheet need not be interrupted; rather, the system automatically calibrates itself constantly. For example, the measuring image of at least one outer receiver can be used for this purpose, which reproduces a border area of the flat-glass substrate but simultaneously also covers an area next to the flat-glass substrate in which light from the light source is incident on the receiver without passing through the glass. Thus, a reference value with a defined calibration value for a transmission of 100% is available to this outer receiver from a zero measurement, with which this receiver can be calibrated. This also applies to a second, opposite outer receiver at the other edge of the glass sheet, which may also be calibrated in this manner. Based on these two outer receivers, the measuring system can then be calibrated by receivers positioned further inward in a step-by-step alignment with the respectively adjacent measuring system. The overlapping of the measuring images of the individual receivers already mentioned above is advantageous for this alignment. In addition to its own data, each receiver thus also has at its disposal data for an overlapping area from at least one adjacent camera that can be used for an alignment and a calibration. Thus, the reference value determined by one of the two outer receivers in a zero measurement can be incorporated, step by step, into each alignment. A suitable self-calibration of the system can be realized in this manner, which makes the measuring device particularly suitable for use directly in the production process, with variable and extreme environmental influences.

The invention also includes an associated device for determining the transmittance of a flat-glass substrate, comprising a measuring device, with which light of at least one light source can be guided from one side of the flat-glass substrate through the flat-glass substrate to the opposite side of the flat-glass substrate, where it is captured by at least one receiving unit. The device has a data processing unit in connection with the light source and the receiving unit, which is configured for determining the transmittance of the flat-glass substrate by means of a comparison between the intensity of the light emitted by the light source and the light incident upon the receiving unit. In this case, the light source is in this case a surface-like diffuse light source, and the receiving unit comprises at least one spatially resolving receiver, between which the flat-glass substrate can be positioned. The data processing unit is further configured for determining the transmittance in a spatially resolved manner in a partial surface of the flat-glass substrate, which is covered by the measuring image, by evaluating brightness values in the measuring image of the spatially resolving receiver.

Preferably, the device has means for continuously moving the flat-glass substrate and the measuring device relative to one another, wherein the light passage through different partial areas of the flat-glass substrate can be captured with the receiving unit over the course of this movement. Thus, the device is configured for verifying the transmittance within a larger surface of the flat-glass substrate. For example, the measuring device can in this case be stationary, whereas the flat-glass substrate is continuously moved through between the light source and the receiving unit. As was already explained above, the measuring device can thus, in particular, be integrated into a production process, with a continuously produced glass sheet passing through the measuring device in a continuous strip.

In this case, the dimensions of the device are preferably chosen in such a way that the flat-glass substrate, transverse to the direction of the relative movement between the measuring device and the flat-glass substrate, has an extent with the width B that is less than the width b of the light source in the same direction. Typical widths for flat-glass substrates are in the order of magnitude of about 3.5 to 4 m, and the light source may protrude over them in each case by 10 cm on two opposite sides, for example.

In order to carry out a line scan, the receiving unit preferably has several spatially resolving receivers, such as cameras, disposed side-by-side. In that case, the data processing unit is configured for combining the measuring images of the receivers into a larger image of a planar area of the flat-glass substrate. Further, the data processing unit is configured for the above-mentioned calibration of the measuring device by means of light of the light source captured by the receiving unit in an area next to the flat-glass substrate without passing through the flat-glass substrate. As a whole, the device, and in particular the data processing unit, are therefore configured for carrying out one or more embodiments of the method according to the invention.

BRIEF DESCRIPTION OF THE SEVERAL VIEWS OF THE DRAWINGS

Other advantages, special features and expedient further developments of the invention are apparent from the dependent claims and the following presentation of preferred embodiments with reference to the illustrations.
In The Drawings

DESCRIPTION OF SPECIFIC EMBODIMENTS OF THE INVENTION

The invention utilizes the principle of the quantitative measurement of the transmittance as a ratio of the intensity of a light beam after its passage through the medium to be measured to that of the incident light beam. For this purpose, it is necessary to know or measure the intensity before and after passing through the obstacle in a measuring device. The fundamental components of an exemplary embodiment of a system with such a measuring device are explained below with reference to the schematic illustrations of FIGS. 1 and 2.

Figure 1:
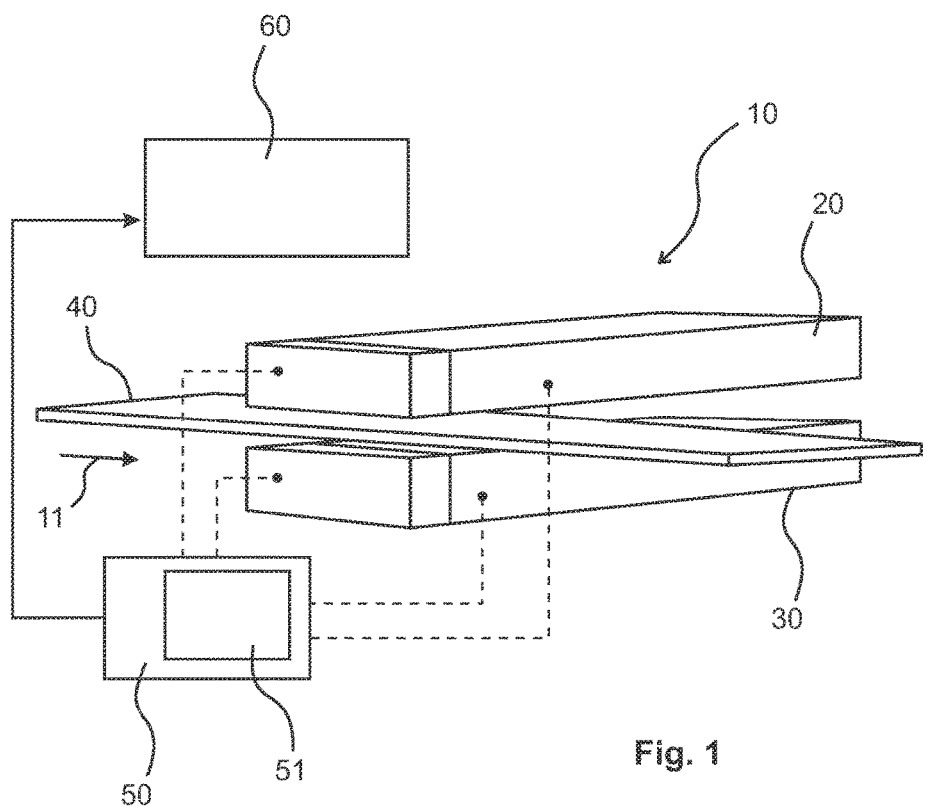
FIG. 1: shows a schematic view of the components of a system with a measuring device for carrying out the method according to the invention.

In this case, the measuring device 10 of the exemplary embodiment of FIG. 1 comprises a surface-like diffuse light source 20. The latter may also be formed by an LED panel with a plurality of light-emitting diodes 21 under a light-transmissive, plate-shaped diffuser 22 (also see FIG. 2). The diffuser 22 may be configured as a film, for instance. Such a panel substantially consists of a circuit board on which light-emitting diodes (LEDs), for example of the SMD type, are mounted in a two-dimensional array. In particular, the LEDs are white-light diodes. A white-light LED may be realized, for example, by a blue LED with a conversion layer based on phosphorescence. These white-light diodes can be supplemented with LEDs generating monochromatic light of different wavelengths. For example, yellow, green, red and/or blue LEDs may be mounted on the same panel. The selection of wavelengths of the LEDs in this case particularly depends on which spectral range is considered relevant for finding a potential impurity.

Within a light wall 20 configured as a light matrix or illuminating matrix, the LEDs are disposed in uniform rows, for example. However, the light-emitting diodes may also be disposed offset relative to one another, or in other special patterns. In particular, an arrangement in hexagonal grids has proved to be useful. The distance between the individual LEDs may suitably be in the order of magnitude of 1 to 4 cm, in particular about 2 cm. An LED panel may in this case comprise about 1000 LEDs, for example. Preferably, each LED is individually controllable, or groups of LEDs can be controlled separately from one another. Preferably, the intensity of the light source 20 is flexibly adjustable, which may take place via a hardware-based current regulation of the LEDs, for example. Advantageously, however, a software-based pulse-width modulation is used (PWM control).

Furthermore, both patterns varying over time and light with different discrete spectra—corresponding to the mounting of different LEDs—may be produced by means of the possible individual control of the LEDs. In this case, a selection of the LEDs best suited for the specific measurement purpose may take place.

The surface-like light source 20 configured in this manner is disposed above a flat-glass substrate 40, for instance, so that the glass is homogeneously illuminated from above. As a further part of the measuring device 10, a receiving unit 30, which comprises at least one spatially resolving receiver in the form of, for example, a camera, is located underneath the flat-glass substrate 40. However, the arrangement of the surface-like diffuse light source 20 and the receiving unit 30 may also be reversed, so that the light source 20 is located underneath and the receiving unit 30 above the glass to be inspected.

Figure 2:
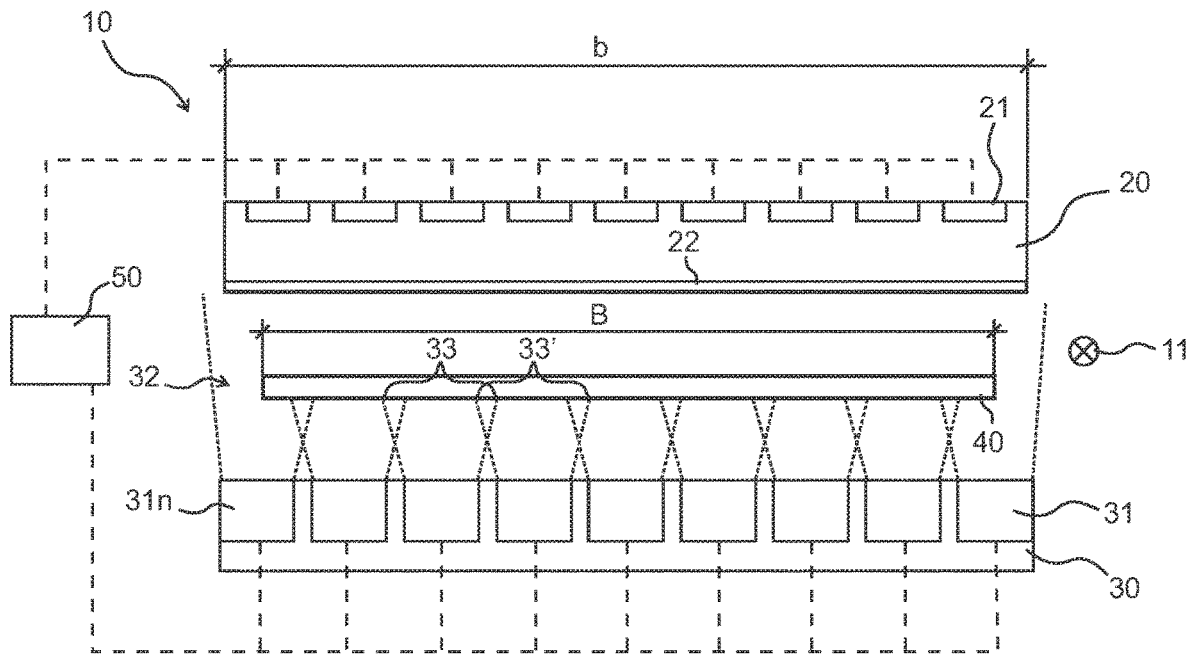
FIG. 2: shows a schematic cross-section through a light source, a flat-glass substrate and a receiving unit.

Preferably, several cameras 31, . . . , 31n are disposed side-by-side, as is also apparent from the cross-section of FIG. 2. In this case, the glass sheet 40 has an extent of the width B transverse to the direction 11 of its movement. By means of a receiving unit 30 with several cameras 31, . . . , 31n disposed side-by-side, a strip-shaped image of the passing flat-glass substrate 40 over its entire width B can be prepared from the images of these cameras. Thus, the receiving unit 30 is so wide, or has so many receivers disposed side-by-side, that the glass sheet 40 can be captured in its entire width B. Accordingly, the light source 20 is also configured in such a way that it is capable of uniformly transmitting light through the entire width B of the flat-glass substrate 40. In this way, a line scan of the glass sheet 40 over its entire width B can be generated by verifying the transmittance in a strip extending over the entire width of the flat-glass substrate. Preferably, the measuring images in the plane of the glass sheet, which can be captured by one camera each, overlap in this case. By way of example, FIG. 2 shows two overlapping areas/measuring images 33 and 33' of two cameras situated next to one another.

For example, the flat-glass substrate 40 is a glass sheet moving in the direction of the arrow 11 through the measuring device 10. Thus, the measuring device 10 with the light source 20 and the receiving unit 30 is stationary in this exemplary embodiment, whereas the glass sheet 40 to be inspected moves relative to the measuring device 10. In this case, the glass is not yet cut into glass plates, but is a continuously produced endless sheet running through the measuring device 10, as it is typically produced in float-glass or structural-glass plants. However, the invention may also be used in glass panes already cut to size.

In this case, the measuring device 10 may also be configured so as to be movable, and may be moved across different areas of a flat-glass substrate, for example, which is then stationary or is also moved simultaneously. Both in the stationary and the movable version, the measuring device 10 can be configured in the form of a portal with an upper and a lower side, between which the flat-glass substrate to be inspected can be positioned.

The light source 20 is operated in a pulsed manner, with the cameras of the receiving unit 30 being synchronized to this quasi-stroboscopic operation. In this case, the flash rate of the light source 20 is, for example, in the range of a few 10 to 100 Hertz, and the flash duration in the microsecond range. Typically, the shutter times of the cameras are longer than the flash duration of the light source. At least for this synchronization, the comparison of emitted and received light intensity and for the determination of the transmittance, the light source 20 and the receiving unit 30 are connected to a data processing unit 50. In particular, the data processing unit 50 is configured for determining the transmittance of a partial surface of the glass sheet in a spatially resolved manner and preferably also verify or assess it based on the target value, based on the intensity of the light of the light source 20 and brightness values for the light received by the spatially resolving receivers 31, . . . , 31*n*.

The data processing unit 50 further comprises an image processing unit 51, which is preferably capable of preparing an image of a captured partial surface of the flat-glass substrate from the images of the cameras. The image processing unit 51 further comprises means for carrying out image editing based on the measuring images of the individual receivers of the receiving unit, which, in particular, also includes an averaging process.

In turn, the data processing unit 50 may be connected with a control unit 60 for the production process within which the flat-glass substrate is produced. When the transmittance of the substrate deviates from a target value, the data processing unit 50 may notify the control unit 60 of this, which then may register the substrate as unsuitable and/or change parameters of the production process in order to bring the transmittance back into the desired range.

In this case, the width b of the light source 20 preferably exceeds the width B of the flat-glass substrate 40. This also applies for the width of the receiving unit 30 or the maximum area that can be imaged by the cameras of the receiving unit 30. In this case, as can be seen in FIG. 2, an outer area 32 is respectively provided to the left and to the right next to the glass sheet 40, within which light of the light source 20 can be incident upon an outer camera 31*n* of the receiving unit 30 without passing through the substrate 40. These areas without light passage through the flat-glass substrate may be used as zero measurement for a calibration of the measuring device 10.

The suitable distance between the LED panel 20 and the plate-shaped diffuser 22 is strongly dependent upon the selected type of diffuser and its properties. For example, it may be in the order of magnitude of 5 to 20 cm, in particular about 10 cm. A distance between the diffuser and the flat-glass substrate of 15 to 45 cm, in particular about 30 cm, has proved to be advantageous, whereas the distance between the receiving unit and the flat-glass substrate as an object distance may be in the order of magnitude of 70 to 150 cm, in particular about 110 cm. This distance is strongly dependent upon the camera sensor and the lens of the camera. Further, the distances between the flat-glass substrate and the components of the measuring device are relevant due to the fact that a measurement is intended preferably on the still-warm substrate, in particular even while the production process is running. Thus, the measuring device is disposed opposite to a glass strip having a temperature of at least 40 to 45° C. However, its temperature may also be significantly above 100° C. The hardware must be adapted to these conditions.

In addition to the above-mentioned hardware, the invention also includes the associated software. The latter is primarily composed of the software for controlling the light sources and receivers, software for evaluating the determined data, and an adapted calibration algorithm. The data processing unit 50 processes the measurement data and is able to forward the corresponding information to the control unit 60 of the production plant or to quality assurance, for example. In this case, the real time behavior of the system is of particular significance, and the high data rates produced during the use of cameras need to be optimized. The very substantial data volume captured by the cameras may be reduced, for example, by pre-evaluation. In particular, this makes it possible to be able to transmit the available measurement data via standard interfaces (LAN, WLAN, CAN bus, etc.) to processing systems without the occurrence of bandwidth issues.

The basic measuring process used for determining or verifying the transmittance of the flat-glass substrate 40 is based on the known wavelength of the light of the light source 20 and the known spectrum of the flat-glass substrate. The glass sheet 40 constitutes an obstacle for the propagation of the light of the light source 20. The transmittance $\tau$ describes the proportion of the transmitted luminous flux relative to the incident luminous flux captured by a camera of the receiving unit 30. If $I_o$ is the intensity of the incident light, and $I_p$ is the intensity of the light behind the glass sheet, then $\tau = I_p/I_o$.

The losses are the result of reflection on the surface and absorption when passing through the glass sheet. In this case, absorption and thus also transmission fundamentally depend on the composition of the glass and its thickness. As a rule, the light sources that play a role in everyday life (sun) are not monochromatic but contain light with different wavelengths. In this case, the transmittance is wavelength-dependent.

In order to determine the transmittance in a continuous spectrum, a light source with the corresponding spectrum is usually required. Using a monochromator, it is possible to adjust the spectrum and determine the transmission for each wavelength. However, the limited temporal resolution is disadvantageous in this case. Furthermore, such a process takes too long to integrate it into an inline inspection of a glass strip passing through continuously. Therefore, it may be advantageous to limit the relevant part of the spectrum with respect to the intended application of the glass. For a robust method for use in production, it has proved to be advantageous, for example, if a limitation to a discrete spectrum is provided which can be realized by monochromatic light sources 20 within the light wall. This may be sufficient for quality assurance. The limitation to selected wavelengths is also advantageous in that interfering influences, particularly due to extraneous light, are easier to eliminate.

In this case, it is necessary to define corresponding representative wavelengths, taking into account the solar spectrum and the spectral characteristics of the various solar cell types, and realize them with the LEDs of the light source 20. The receiving unit 30 is then tuned to these wavelengths.

The refresh rate is in this case determined for a quasi-continuous measurement depending on the travel speed of the glass sheet.

In addition or as an alternative, it is also possible to carry out a white-light measurement with white-light diodes of the light source 20. Thus, impurities can be found for all included wavelengths which could cause a reduction of the transmittance by means of selective absorption.

With the method according to the invention, the transmittance of a flat-glass substrate 40 can be determined over its entire surface, preferably in a spatially resolved manner. For mere quality assurance, it may possibly suffice if an absolute measurement of the transmittance is replaced by a comparison measurement (deviation from a target). In that case, it is sufficient to generate the reference values by means of material with the desired properties.

In addition to a homogenous planar illumination of the glass sheet by the surface-like light source 20, there is also the option of generating inspection patterns by individually controlling the LEDs. In this manner, the device can be extended also with respect to defect recognition. Together with the targeted triggering of camera shots, different measurements can then be carried out quasi-simultaneously. Using hardware triggers, short light flashes with various properties can be produced. Mention may be made, for example, of a homogeneous illumination, patterns emphasizing individual LEDs, or gray gradients produced by different flash durations of the individual LEDs.

A calibrated measuring system is a fundamental requirement for an exact and reproducible measurement. Therefore, a calibration method is preferably used which can be integrated into the inline measuring method, because flat-glass production is an interruption-free, continuous process. Therefore, the process cannot be interrupted for a calibration of the measuring device. In this case, an intensity regulation of the LED spotlights by means of PWM instead of the conventional current regulation provides a means for being able to arbitrarily adjust and re-adjust the brightness of the light source 20 if required. Furthermore, with PWM, age-related reductions of the light intensity can be compensated individually for each LED in the online calibration method, and a high level of long-term stability of the light source can be ensured.

With a typical sheet width B of 3.5 to 4 meters and measuring equipment both on the upper and the lower side, it is difficult to calibrate the measuring devices in an offline process because this entails considerable conversion effort. In contrast, movable parts, which would also be disadvantageous, would be required for an automated calibration process.

Therefore, in one embodiment, the invention uses an approach for a calibration that gets along without any movable parts. In this case, all of the light sources and cameras used are calibrated in a step-by-step alignment with the neighboring system, wherein the respective outer cameras, due to zero measurements next to the glass sheet, are provided with reference values with defined calibration values. Thus, it is possible to carry out an alignment with a reference system as well as assess the quality of the calibration. With the reference systems on both sides, a faulty calibration that may be produced by instantaneous changes of the glass properties can be excluded.

LIST OF REFERENCE NUMERALS

10 Measuring device
11 Direction of relative movement, direction of movement of glass sheet
20 Light source, light wall, LED panel
21 Light source, light-emitting diode, LED
22 Diffuser
30 Receiving unit
31, 31n Receiver, camera
32 Outer measurement area
33, 33' Measuring image
40 Flat-glass substrate, glass sheet
50 Data processing unit
51 Image processing unit
60 Control unit of a production plant

What is claimed is:

1. A method for determining the transmittance of a flat-glass substrate with a measuring device, with which light of at least one light source is guided from one side of the flat-glass substrate through the flat-glass substrate to the opposite side of the flat-glass substrate, where it is captured by at least one receiving unit and the transmittance of the flat-glass substrate is determined by means of a comparison between the intensity of the light emitted by the light source and the light incident upon the receiving unit, wherein the light source is a surface-like diffuse light source, and the receiving unit comprises at least one spatially resolving receiver, between which the flat-glass substrate is positioned, and the transmittance is determined in a spatially resolved manner in a partial surface of the flat-glass substrate, which is covered by a measuring image of the spatially-resolving receiver, by an evaluation of brightness values in the measuring image, wherein light of the light source is captured by the receiving unit in at least one area next to the flat-glass substrate without passing through the flat-glass substrate;

wherein the light of the light source captured by the receiving unit without passing through the flat-glass substrate is used for defining a reference value for the calibration of the measuring device; and wherein a measuring image of at least one outer receiver, which reproduces a border area of the flat-glass substrate, also includes an area next to the flat-glass substrate via which this outer receiver obtains a reference value with a defined calibration value and the measuring system of further receivers is calibrated in a step-by-step alignment with the respectively adjacent measuring system.

2. The method of claim 1, wherein the flat-glass substrate and the measuring device are continuously moved relative to one another in such a manner that over the course of this movement, the receiving unit captures the light passage through different partial areas of the flat-glass substrate.

3. The method of claim 2, wherein the measuring device is stationary, whereas the flat-glass substrate is continuously moved through between the light source and the receiving unit.

4. The method of claim 2, wherein the flat-glass substrate has an extent with the width B transverse to the direction of the relative movement between the measuring device and the flat-glass substrate, with the light source transmitting light through the flat-glass substrate over the entire width B and the receiving unit capturing light passing through a strip through the flat-glass substrate extending over the entire width B of the flat-glass substrate.

5. The method of claim 1, wherein in the measuring image of the spatially resolving receiver, an image editing is carried out with includes an averaging process for brightness values over several points of at least a portion of the measuring image, and the transmittance is determined after the image editing of the measuring image.

6. The method of claim 5, wherein the portion of the measuring image used for the averaging process is larger than dimensions of structures in the surface of the flat-glass substrate.

7. The method of claim 1, wherein a verification of the transmittance is carried out by means of a comparison of a transmittance determined by the measuring device with a target transmittance.

8. The method of claim 1, wherein the receiving unit has several receivers, which are configured for capturing light of the light source and whose measuring images are combined into an image of a planar area of the flat-glass substrate by an image processing unit.

9. The method of claim 8, wherein the receivers are disposed next to one another, and their measuring images are combined into an image of a strip of the flat-glass substrate extending over the entire width B.

10. The method of claim 8, wherein the measuring images of the receivers overlap in some areas.

11. The method of claim 1, wherein the calibration of the measuring device takes place continuously during the verification of the transmittance.

12. A device for determining the transmittance of a flat-glass substrate, comprising a measuring device, with which light of at least one light source can be guided from one side of the flat-glass substrate through the flat-glass substrate to the opposite side of the flat-glass substrate, where it is captured by at least one receiving unit, and the device has a data processing unit in connection with the light source and the receiving unit, which is configured to determine the transmittance of the flat-glass substrate by means of a comparison between the intensity of the light emitted by the light source and the light incident upon the receiving unit, wherein the light source is a surface-like diffuse light source, and the receiving unit comprises at least one spatially resolving receiver, between which the flat-glass substrate can be positioned, and the data processing unit is further configured for determining the transmittance in a spatially resolved manner in a partial surface of the flat-glass substrate, which is covered by a measuring image of the spatially-resolving receiver, by an evaluation of brightness values in the measuring image, wherein the receiving unit has several spatially resolving receivers disposed side by side;

wherein the device is configured such that light of the light source is captured by the receiving unit in at least one area next to the flat-glass substrate without passing through the flat-glass substrate;

wherein the device is configured such that the light of the light source captured by the receiving unit without passing through the flat-glass substrate is used for defining a reference value for the calibration of the measuring device; and wherein the device is configured such that a measuring image of at least one outer receiver of the several spatially resolving receivers, which reproduces a border area of the flat-glass substrate, also includes an area next to the flat-glass substrate via which this outer receiver obtains a reference value with a defined calibration value and the measuring system of further receivers is calibrated in a step-by-step alignment with the respectively adjacent measuring system.

13. The device of claim 12, wherein the device has means for continuously moving the flat-glass substrate and the measuring device relative to one another, wherein the light passage through different partial areas of the flat-glass substrate can be captured with the receiving unit over the course of this movement.

14. The device of claim 13, wherein the measuring device is stationary, whereas the flat-glass substrate is continuously moved through between the light source and the receiving unit.

15. The device of claim 12, wherein the flat-glass substrate, transverse to the direction of the relative movement between the measuring device and the flat-glass substrate, has an extent with the width B that is less than the width b of the light source in the same direction.

\* \* \* \* \*